US011123210B2

United States Patent
Fleming

(10) Patent No.: US 11,123,210 B2
(45) Date of Patent: Sep. 21, 2021

(54) CABLE KNEE BRACE SYSTEM

(71) Applicant: Darren Fleming, Vista, CA (US)

(72) Inventor: Darren Fleming, Vista, CA (US)

(73) Assignee: MOBIUS TECHNOLOGIES, LLC, Ketchum, ID (US)

(*) Notice: Subject to any disclaimer, the term of this patent is extended or adjusted under 35 U.S.C. 154(b) by 0 days.

(21) Appl. No.: 13/867,910

(22) Filed: Apr. 22, 2013

(65) Prior Publication Data

US 2014/0148747 A1    May 29, 2014

Related U.S. Application Data

(63) Continuation of application No. 12/987,084, filed on Jan. 8, 2011, now abandoned, which is a continuation-in-part of application No. 11/744,213, filed on May 3, 2007, now abandoned.

(51) Int. Cl.
   *A61F 5/00* (2006.01)
   *A61F 5/01* (2006.01)

(52) U.S. Cl.
   CPC .... *A61F 5/0123* (2013.01); *A61F 2005/0137* (2013.01); *A61F 2005/0167* (2013.01); *A61F 2005/0179* (2013.01)

(58) Field of Classification Search
   CPC ............ A61F 5/0123; A61F 2005/0167; A61F 2005/0137; A61F 2005/0132; A61F 2005/0134; A61F 2005/0139; A61F 2005/0141; A61F 2005/0146; A61F 2005/0148; A61F 2005/0151; A61F 2005/0153; A61F 2005/0165; A61F 2005/0144; A61F 5/013; A61F 2005/0179; A61F 5/0102; A61F 13/061; A61F 5/01; A61F 5/00; A61F 5/04; A61F 13/062; A61F 5/0106; A61F 5/0109; A61F 5/0118; A61F 5/0125
   USPC ............................... 602/26, 23, 16; 128/882
   See application file for complete search history.

(56) References Cited

U.S. PATENT DOCUMENTS

| | | | | |
|---|---|---|---|---|
| 4,865,024 A | * | 9/1989 | Hensley | A61F 5/0123 602/16 |
| 4,955,369 A | * | 9/1990 | Bledsoe | A61F 5/0123 602/16 |
| 5,599,288 A | * | 2/1997 | Shirley | A61F 5/0123 602/16 |
| 7,662,122 B2 | * | 2/2010 | Sterling | A61F 5/0123 128/882 |
| 2002/0133108 A1 | * | 9/2002 | Jagodzinski | A61F 5/0123 602/16 |

* cited by examiner

*Primary Examiner* — Victoria J Hicks
(74) *Attorney, Agent, or Firm* — Richard T. Black; Foster Garvey PC

(57) ABSTRACT

It is the object of the invention to provide a knee bracing system that bolsters the body's natural ligaments to reduce the knees proneness to injury or re-injury. The invention is a cable system that acts much like the body's natural way that resists the forces that cause excessive joint movement and injury to the ACL and or MCL. As the leg travels through the range of motion the cables provide external hyper extension, bending, and rotation support preventing the tibia bone from moving forward (hyper extending) or twisting (lateral rotation) and or laterally bending with respect to the femur.

7 Claims, 9 Drawing Sheets

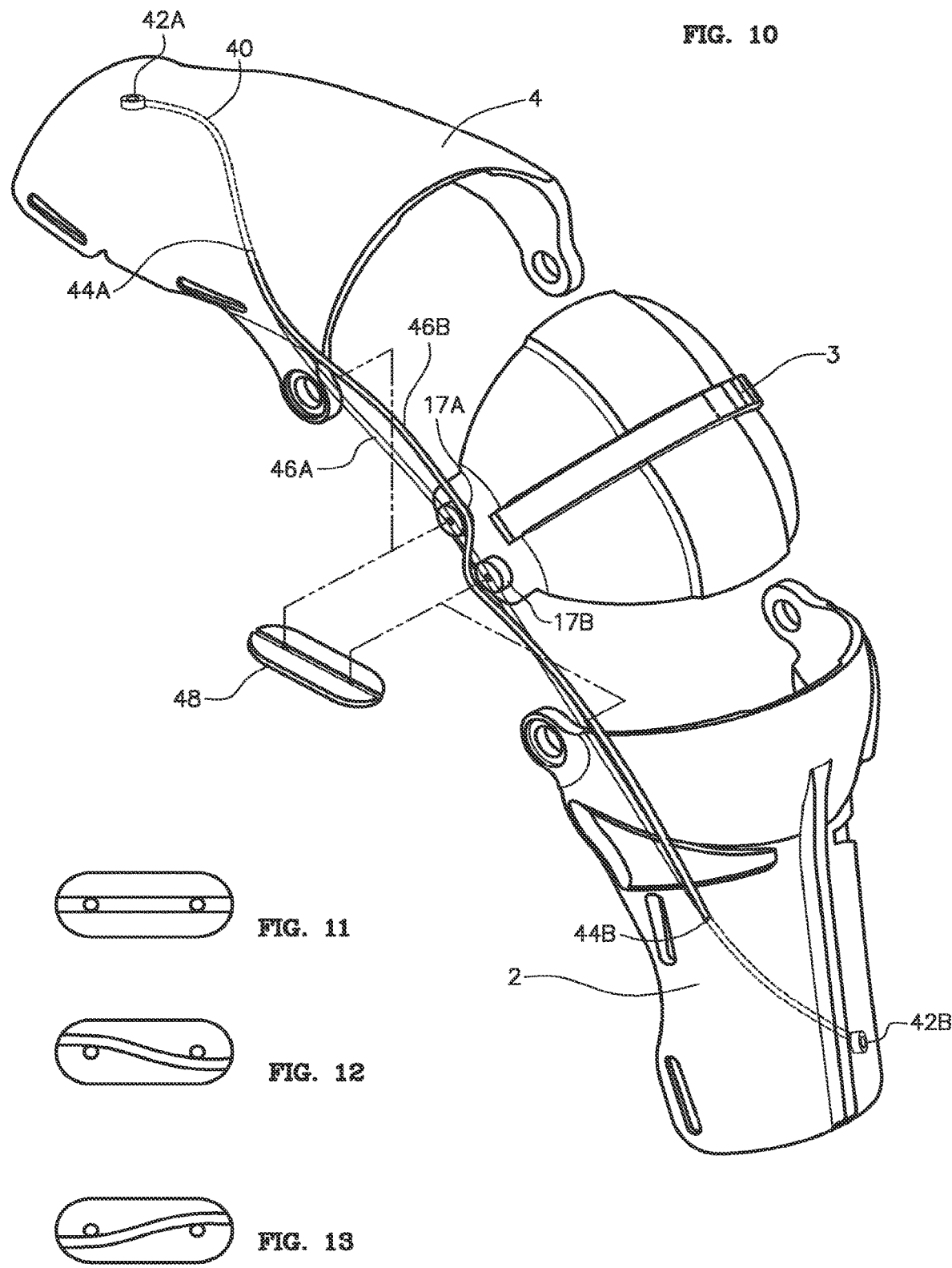

CABLE KNEE BRACE SYSTEM

PRIORITY CLAIM

This application is a continuation of U.S. patent application Ser. No. 12/987,084 filed on Jan. 8, 2011, which is a continuation-in-part of U.S. patent application Ser. No. 11/744,213 filed on May 3, 2007.

BACKGROUND OF THE INVENTION

The human knee is a complex mechanism that is highly vulnerable to injury in sports like football, hockey, skiing, snowboarding, and motocross. In these kinds of physically demanding sports the Anterior Cruciate Ligament (ACL) and Medial Collateral Ligaments (MCL) are commonly injured. The ACL controls forward movement of the tibia relative to the femur (hyper extension) and lateral rotation of the tibia with respect to the femur (over rotation). The MCL controls lateral movement of the tibia with respect to the femur. Hyper extending the leg and or laterally rotating or twisting or laterally bending of the leg can tear the ACL and/or MCL. The ACL regulates the amount of movement the tibia has with respect to the femur both in forward movement, and lateral rotation. When the leg reaches full extension the ACL becomes taut and limits the knee from hyper extending or over rotating laterally.

The MCL regulates how much the tibia can bend laterally with respect to the femur. The MCL becomes taut when a lateral force is applied to the leg preventing excessive bending. All too often in sports like motocross the leg is exposed to forces that exceed the ligament's ability to prevent excessive movement in the joint sometimes resulting in the tearing of the ACL and or MCL.

In order for a knee brace to be effective in resisting the excessive movement of the knee joint that tears the ACL and/or MCL, it must provide an effective differential force to the tibia relative to the femur. Because of the large amount of flesh surrounding the tibia bone and femur bone the only way to prevent the leg from over extending or over rotating would be to fix a rigid structure to the bones with some sort of mechanical means such as screws. Of course this would be impractical and undesirable. Not only should a knee brace be practical, it must be comfortable, and most of all effective preventing knee injuries.

Most prior art (conventional) knee brace devices for ligament protection consist of a rigid femoral plate and tibial plate connected by hinges on either side of the knee. The plates are strapped to the leg tightly above and below the knee with straps that encircle the leg. The hinge locks as the leg reaches full extension and the rigid frame and straps act like a splint resisting hyperextension of the leg. There are many variations of the basic rigid hinged brace with differing hinge designs, strapping methods, and materials used. Conventional braces are limited in their effectiveness resisting excessive joint movement that causes injury to the knee. The biggest reason is that the flesh of the leg surrounding the femur and the strapping apparatus deform allowing the leg to hyper extend or rotate. Even when the strapping devices are tightened to the point of discomfort, they have limited effect preventing excessive movement of the knee joint when the leg is subjected to these forces.

It is the object of the invention to provide a knee bracing system that bolsters the body's natural ligaments to reduce the knees proneness to injury or re-injury.

The invention is a cable system that acts much like the body's natural Anterior Cruciate Ligament (ACL) and Medial Collateral Ligaments (MCL). The cables are routed around the knee joint in a way that resists the forces that cause excessive joint movement and injury to the ACL and or MCL. As the leg travels through the range of motion the cables tighten preventing the tibia bone from moving forward (hyper extending) or twisting (lateral rotation) or bending laterally with respect to the femur.

The cable knee brace system of this invention can be tailored or adapted to prior art (conventional) braces increasing their effectiveness.

It is also anticipated by the Applicant that this cable knee brace system can be adapted to the elbow to prevent the arm from hyper extending. A humorous plate would substitute for the femoral plate 4, a radius plate would substitute for the tibial plate 2, and bicep plate would substitute for the femoral back plate 5 creating the differential resistive force across the elbow joint preventing hyperextension of the arm.

BRIEF DESCRIPTION OF THE DRAWINGS

FIG. 10 is an exploded isometric view of the individual parts of the secondary cable knee brace system.

FIG. 11 is an inside elevation/side view of the secondary cable guide plate that guides the secondary cable through the pivot points.

FIG. 12 is an inside elevation/side view of an alternate cable guide plate that guides the secondary cable under and over the pivot points.

FIG. 13 is an inside elevation/side view of another alternative cable guide plate that guides the secondary cable over and under the pivot points.

DETAILED DESCRIPTION

Figure 1:
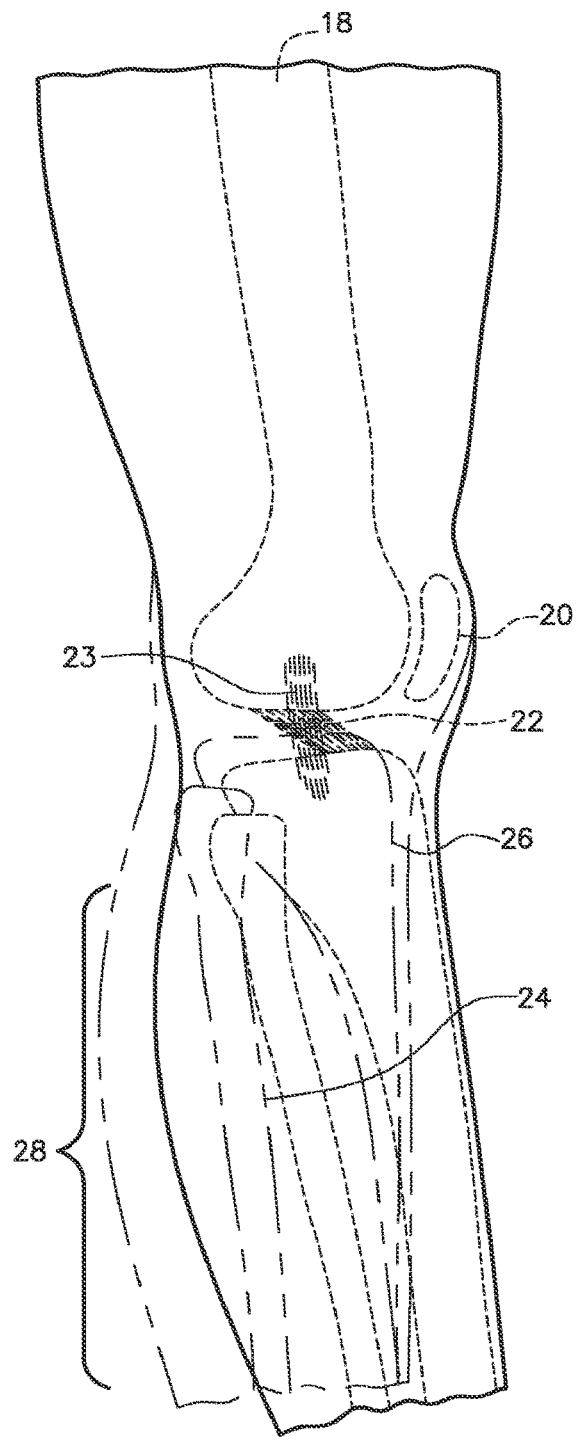
FIG. 1 is an outside elevation/side view of a right leg showing normal fully extended and hyper extended (tearing ACL) views.
Figure 2:
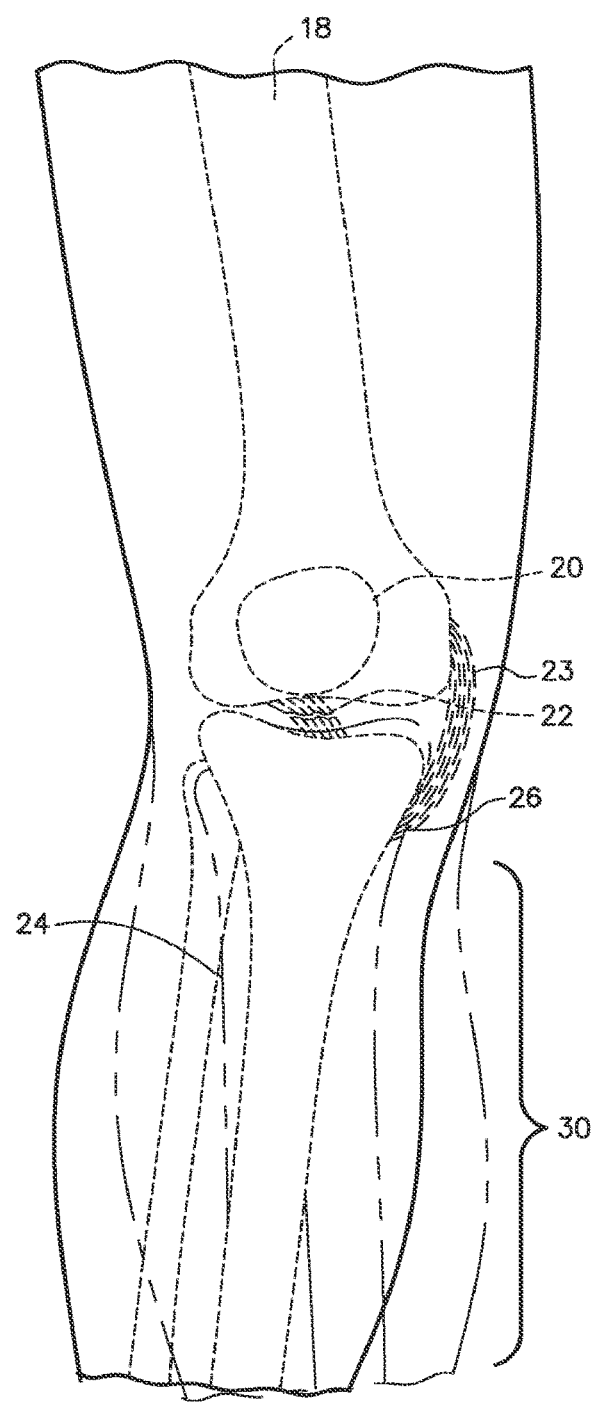
FIG. 2 is a top/front view of the right leg fully extended showing normal and laterally rotated or laterally bent (tearing ACL and or MCL) views.

To be effective preventing injuries to the ACL 22 and or MCI 23 a knee brace must prevent the tibia bone 26 from moving forward (hyper extending), see FIG. 1, or laterally bending and or rotating (twisting), see FIG. 2, with respect to the femur bone 18. The patella 20 and fibula bone 24 are shown for completeness. The knee brace of this invention as best shown in FIGS. 3, 4, 5, 6, 7, 8, 9, and 10, which like references refer to like elements throughout the several views, introduces a novel cable system that more effectively prevents hyper extension, lateral bending and or lateral rotation of the knee joint.

Figure 3:
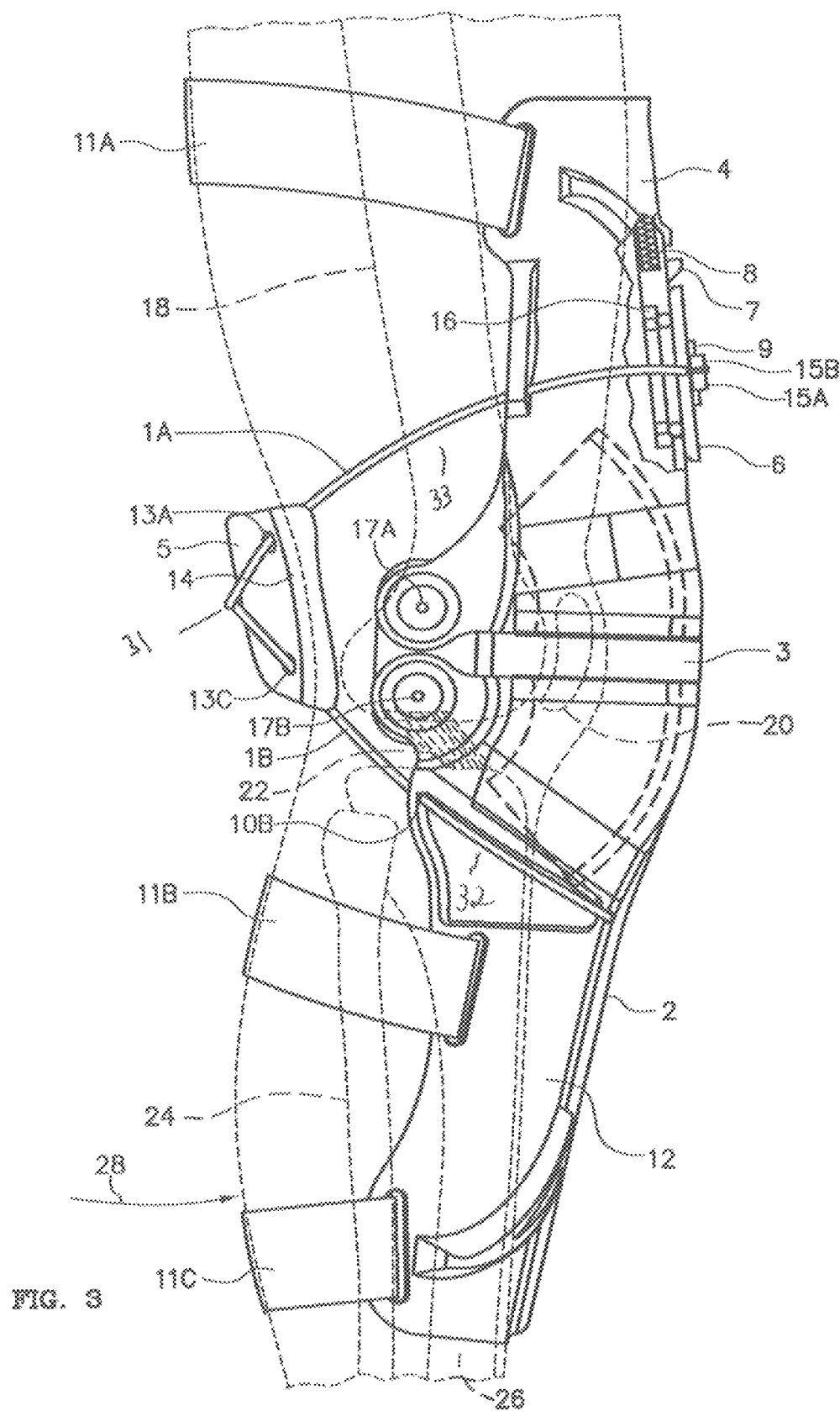
FIG. 3 is an outside elevation/side view of the right leg fully extended showing the primary cable resisting hyperextension of the leg.
Figure 4:
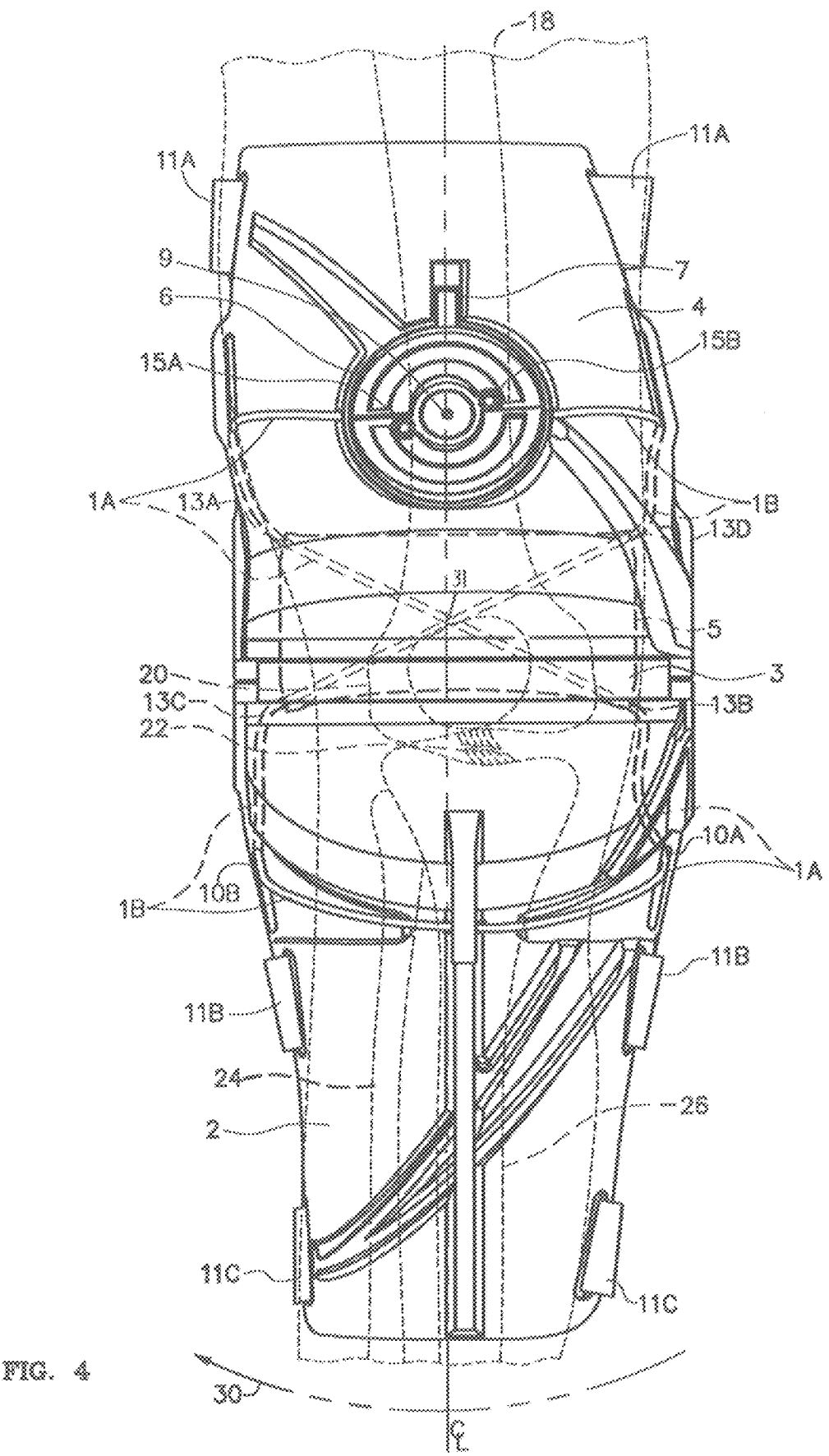
FIG. 4 is a top/front view of the right leg fully extended showing the primary cable resisting lateral rotation of the leg.
Figure 5:
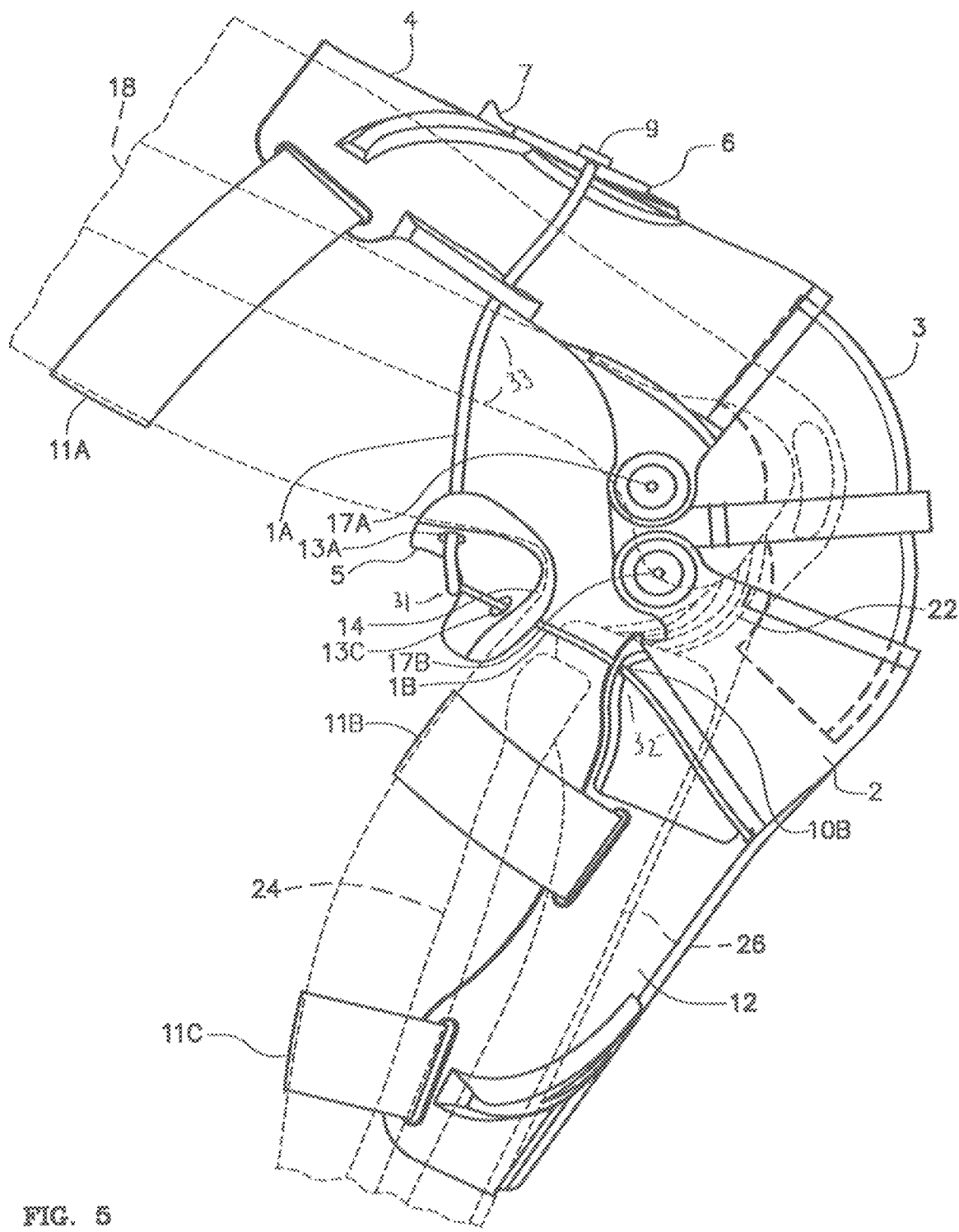
FIG. 5 is an outside elevation/side view of the right leg in the flexed position showing the primary cable knee brace system.
Figure 7:
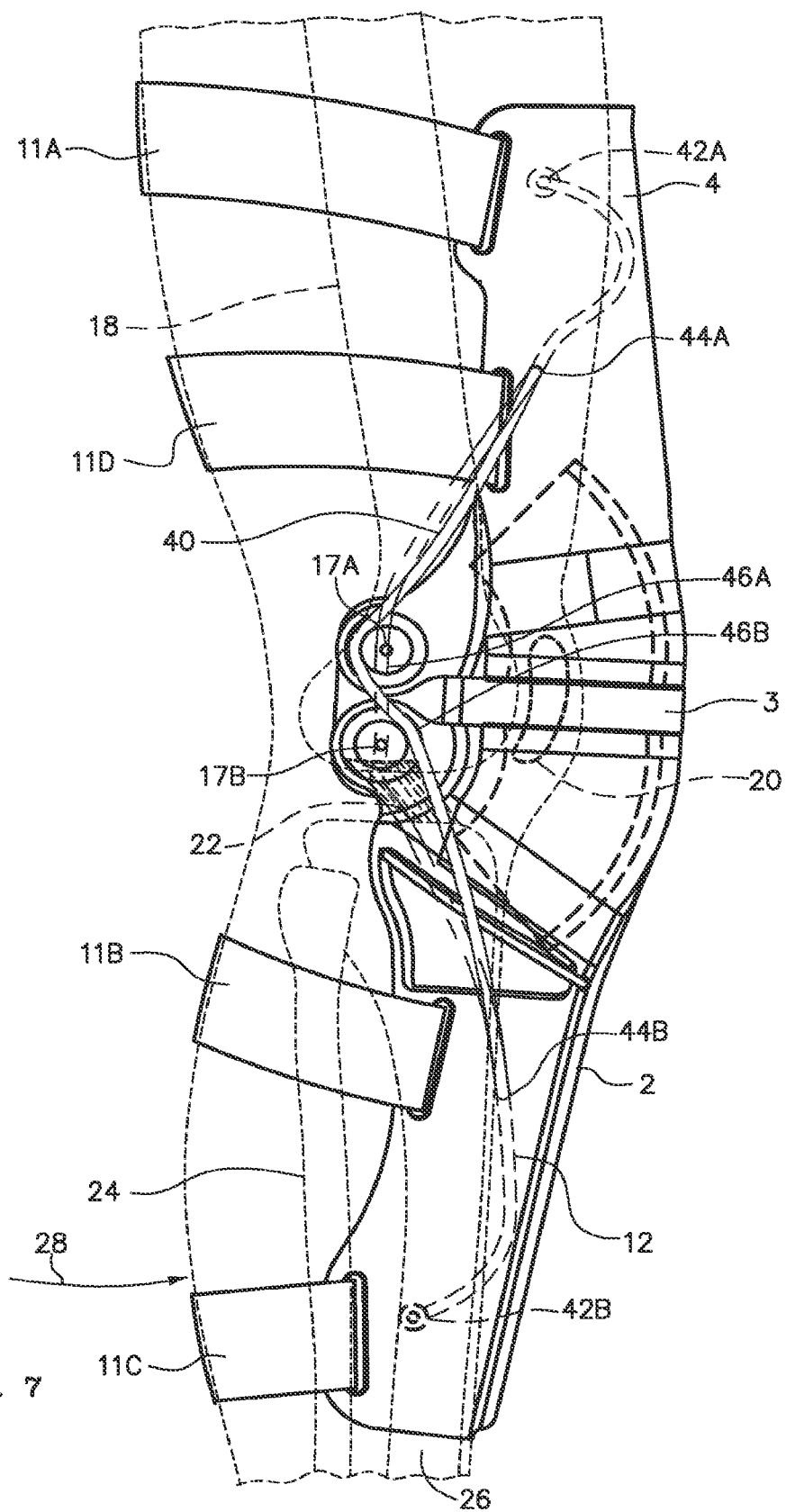
FIG. 7 is an outside elevation/side view of the left leg fully extended showing the secondary cable resisting hyper extension of the leg.
Figure 8:
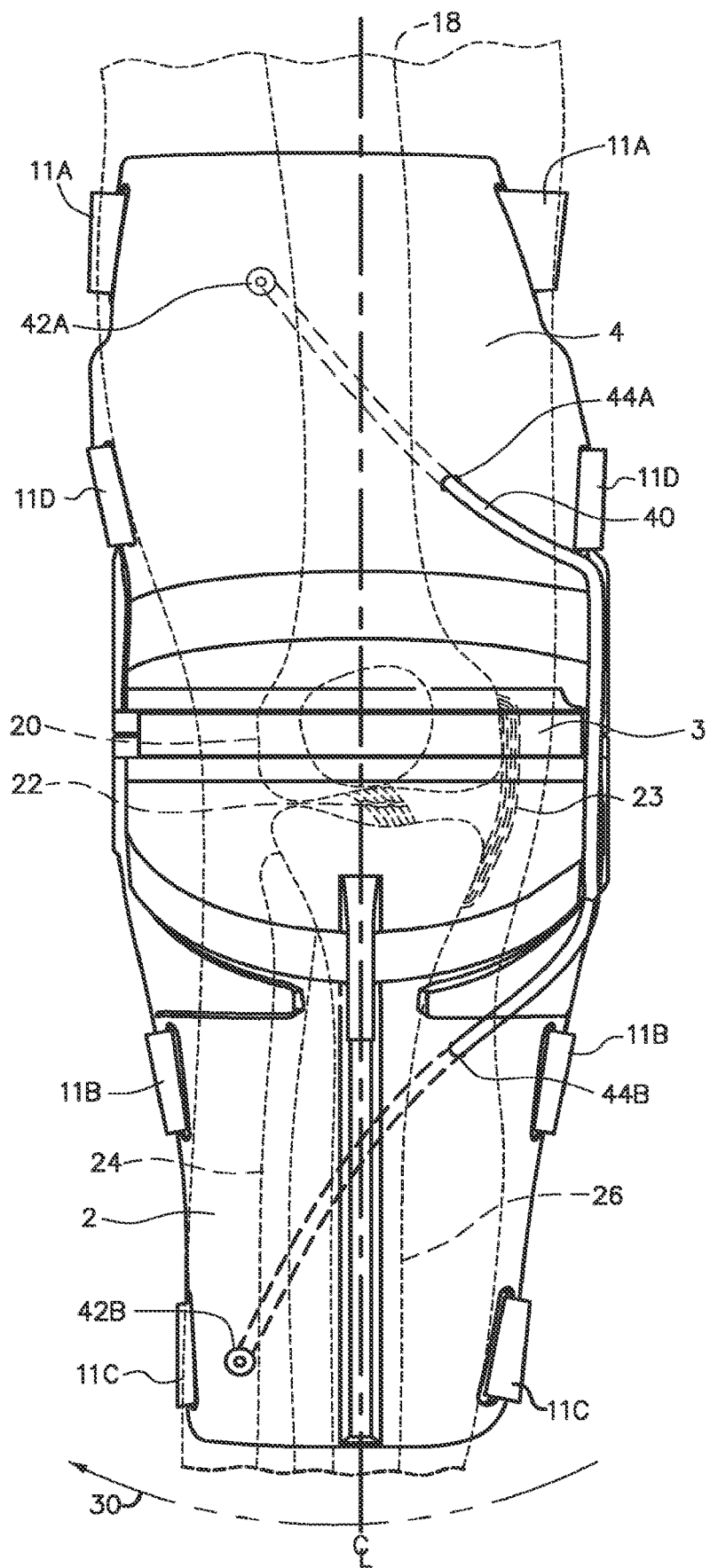
FIG. 8 is a top/front view of the right leg fully extended showing the secondary cable resisting lateral rotation and or lateral bending of the leg.
Figure 9:
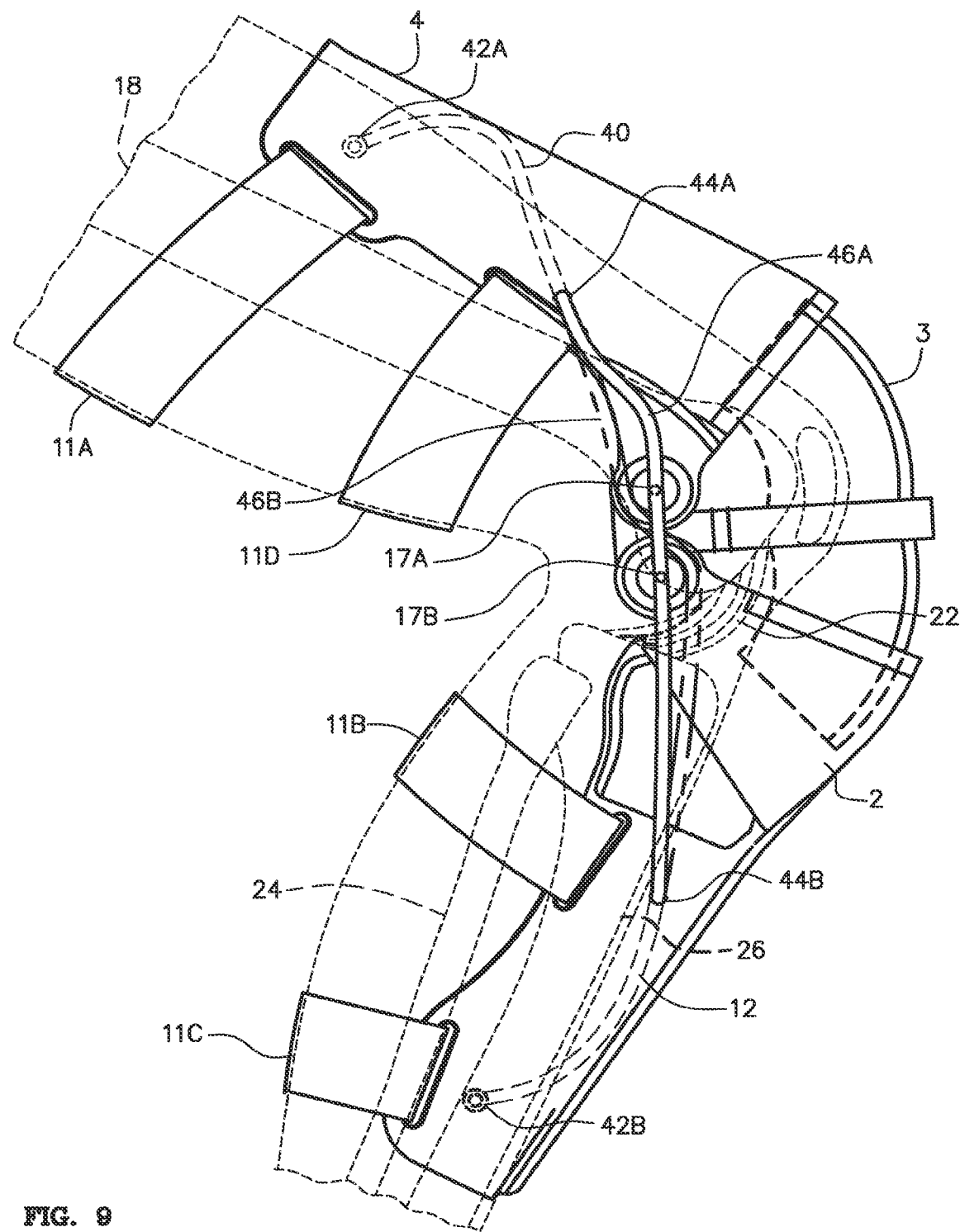
FIG. 9 is an outside elevation/side view of the left leg in the flexed position showing the secondary cable resisting lateral bending or lateral rotation.

FIG. 3 shows the primary cable system of this invention creating an effective differential force to the tibia 26 relative to the femur 18 and reinforcing the ACL 22. When the primary cable 1 of this system is properly tensioned the brace acts like the body's own ACL 22 becoming taut as the leg extends resisting the forward movement of the tibia bone 26, with respect to the femur bone 18. FIG. 4, shows the primary cable system of this invention resisting the lateral rotation of the tibia bone 26, with respect to the femur bone 18. FIG. 5 shows the primary cable system of this invention when the leg is flexed. Because the tibial plate 2 moves further away from the femoral plate 4 as the leg extends the primary cable 1 becomes progressively tighter as the leg approaches full extension, as shown in FIG. 3. When a hyper extension force 28 is applied to the leg as shown in FIG. 3 the tibial plate 2, patellar plate 3, and femoral plate 4 are compressed together as the primary cable 1 comes under progressively more tension. The tensile force in the primary cable 1 pulls down on the tibial plate 2, and up on the back plate 5 creating the differential resistive force across the knee joint preventing hyper extension of the leg. FIG. 7 shows the secondary cable system of this invention creating an effective differential force to the tibia 26 relative to the femur 18 and reinforcing the ACL 22 and MCL 23. As the leg extends the secondary cable 40 resists the forward movement of the tibia bone 26, with respect to the femur bone 18. FIG. 8, shows the secondary cable 40 resisting the lateral bending and or lateral rotation of the tibia bone 26, with respect to the femur bone 18. FIG. 9 shows the secondary cable system of the invention when the leg is flexed and the secondary cable 40 resisting lateral bending and lateral rotation throughout the legs range of motion. As the leg extends the patellar plate 3 acts like a hinge for the femoral plate 4 and tibial plate 2 rotating about pivot points 17a and 17b, respectively, approximating the knees flexion-extension movement.

When a lateral rotation force 30 is applied to the leg as shown in FIG. 4 the tibial plate 2, patellar plate 3, femoral plate 4, and back plate 5 are held rigid by the tension developed in the primary cable 1. The tensile forces in primary cable 1 cross behind the leg creating cable cross over point 31 as they pass through back plate 5 resisting rotation and bending across the knee joint preventing the leg from laterally bending or rotating. When a lateral bending or lateral rotation force is applied to the leg as shown in FIG. 8 the tibial plate 2, patellar plate 3, and femoral plate 4 are held rigid by the tension developed in the secondary cable 40. The tension in the secondary cable 40 prevents the brace from bending across the knee joint preventing the leg from laterally bending or rotating.

This invention comprises of a primary cable 1 and secondary cable 40 that can be made of any flexible material with a sufficiently high tensile strength. A tibial plate 2 configured to receive a shin portion of the leg that could be made of any rigid or semi rigid material is shaped to conform to the tibia bone 26, beginning just below the knee and ending approximately at the midpoint of the tibia bone 26. The tibial plate 2 is held in position with elastic straps 11b and 11c. Foam padding 12 is attached to the underside of the tibial plate 2 for comfort and to provide a firm grip on the individuals' tibia bone 26. A patellar plate 3 that could be made of any rigid or semi rigid material connecting the tibial plate 2 to the femoral plate 4. A femoral plate 4 configured to receive a thigh portion of the leg that could be made of any rigid or semi rigid material is located on top of the thigh from just above the knee to approximately mid femur 18 and is held in position with elastic strap 11a and 11d. And back plate 5 that could be made of any rigid or semi rigid material located behind the leg and just above the knee joint to keep the cable 1 in the proper location, firmly holding the femur bone 18 as the differential force of the primary cable 1 is transmitted across the joint. Foam padding 14 is attached to the inside of the back plate 5 to help spread the force of the primary cable 1 comfortably to the leg. A cable tensioner dial 6 and locking/release button 7 with spring 8 are attached to the femoral plate 4 with retainer screw 9. These could be made from any metal or rigid material that will withstand the forces required to keep the primary cable 1 locked in place during use. Other cable tensioning and locking mechanisms could be used, but the dial tensioning and locking system gives a very wide range of fine tuned cable adjustability and ease of use.

Figure 6:
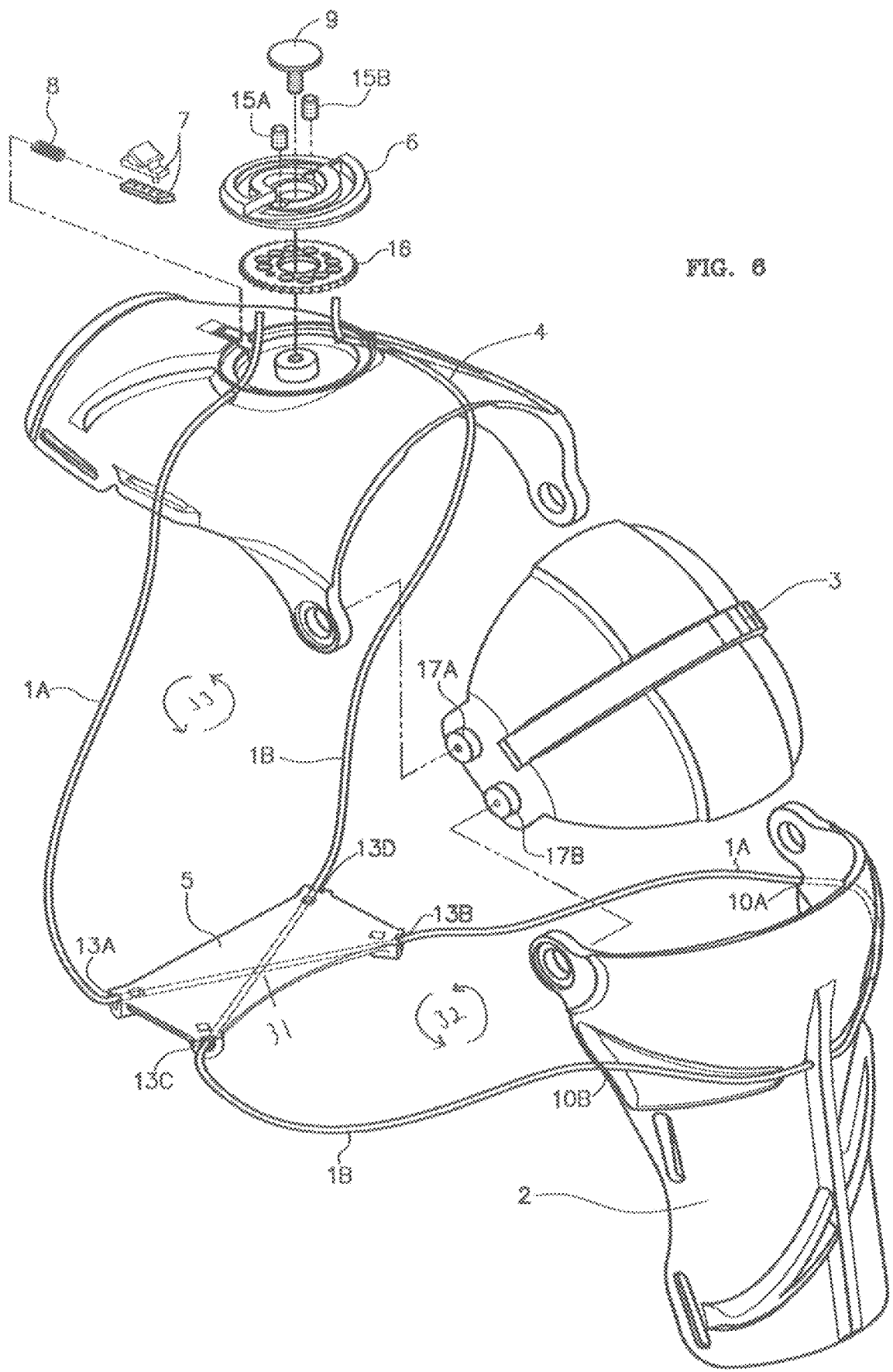
FIG. 6 is an exploded isometric view showing the individual parts of the primary cable knee brace system.

The fundamental element of this invention is the routing of the cables. As best shown in FIG. 6 primary cable 1 begins attached to femoral plate 4 by first cable connector 15 a, crosses behind the leg through first cable guide hole 13 a and second cable guide hole 13 b in back plate 5, and attaches to the opposite side of tibial plate 2 with clamping screw 10 a. The primary cable 1 then loops over the leg attaching to the other side of tibial plate 2 with clamping screw 10 b. From clamping screw 10b the primary cable 1 again crosses behind the leg through third cable guide hole 13 c and fourth cable guide hole 13 d in back plate 5, creating cable cross over point 31, and attaches to the opposite side of femoral plate 4 by second cable connector 15 b. The segments of the cable extending from the cable cross over point 31 to the tibial plate portion of the brace, through clamp 10a and 10b and returning to the cable cross over point 31 forming the tibial control loop or portion 32 of the cable. The segments of cable extending from the cable cross over point 31 to the femoral cable connectors 15a and 15b forming the femoral control loop or portion 33 of the cable. As best shown in FIG. 10 secondary cable 40 begins attached to the outside, or collateral side, of the femoral plate 4 by the femoral cable connector 42 a and runs through the femoral cable guide hole 44 a. The secondary cable 40 crosses femoral pivot point 17 a and tibial pivot point 17 b through cable guide plate 48. From there the secondary cable 40 runs through tibial plate guide hole 44 b and attaches to the outside, or lateral side, of the tibial plate 2 by the tibial cable connector 42 b, completing the route.

The cables could be made up of individual segments connected together to form the completed routing. For example, first primary cable segment 1a and second primary cable segment 1b can be connected together with tibial plate 2 to complete the loop. The segments of the cable extending from the cable cross over point 31 to the tibial plate portion of the brace and returning to the cable cross over point 31 form the tibial control loop portion 32 of the cable. The segments of cable extending from the cable cross over point 31 to the femoral plate portion of the brace and returning to the cable cross over point 31 forming the femoral control loop portion 33 of the cable. FIG. 6, for example, illustrates these control loop portions 32 and 33. First primary cable segment 1a begins attached to femoral plate 4 by first cable connector 15a, crosses behind the leg through the first cable guide hole 13a and second cable guide hole 13b in back plate 5 and attaches to the opposite side of tibial plate 2 with clamping screw 10a. Without having to loop over the leg, the second primary cable segment 1b is attached to the opposite side of tibial plate 2 with clamping screw 10*b*. From clamping screw 10*b* the second primary cable segment 1*b* crosses behind the leg through the third cable guide hole 13*c* and fourth cable guide hole 13*d* in back plate 5 and completes the loop by attaching to the opposite side of femoral plate 4 with cable connector 15*b*.

The primary cable 1 is adjusted by turning the cable tensioner dial 6 taking up the excess primary cable 1 length. The primary cable 1 is automatically locked into place by the ratcheting gears 16 on the cable tensioning dial 6 and spring 8 actuated locking/release button 7. The button 7 is also used to release the tension in primary cable 1 for installation and removal of the brace.

While an infinite number of secondary cable routings across the pivot points are possible, directly through the pivot points as shown in 46*a* is most desirable to achieve optimum tension on the secondary cable 40 throughout the leg's full range of motion. FIG. 11 shows a cable guide plate which guides the cable directly through the pivot points, secondary cable routing 46*a*, as described above. Alternate secondary cable guide plate configurations as shown in FIGS. 12 and 13 could be used guide the secondary cable around the pivot points. For example, alternate secondary cable routing 46*b* could be achieved using the cable guide plate shown in FIG. 13 which guides the secondary cable 40 over, or to the fore of, femoral pivot point 17*a* and under, or to the aft of, tibial pivot point 17*b*.

While the invention has been described and illustrated with regard to the particular embodiment, changes and modifications may readily be made, and it is intended that the claims cover any changes, modifications, or adaptations that fall within the spirit and scope of the invention.

The invention claimed is:

1. A functional knee brace to be worn on a leg comprising;
   a semi-rigid femoral plate configured to receive a first thigh portion of the leg and including a thigh strap, the semi-rigid femoral plate being rotatable about a femoral point and having a cable guide;
   a semi-rigid tibial plate configured to receive a shin portion of the leg, the semi-rigid tibial plate being rotatable about a tibial pivot point and having a cable guide;
   a back plate capable of being located behind the leg and just above a knee joint, and wherein the back plate cooperates with the semi-rigid femoral plate and the semi-rigid tibial plate, the back plate having a cable guide;
   a first substantially inelastic cable, wherein the first substantially inelastic cable is routed from the semi-rigid femoral plate, the first substantially inelastic cable traveling around the back plate, the first substantially inelastic cable traveling around and over the top of the semi-rigid tibial plate, the first substantially inelastic cable crossing over itself at a crossover point at the back plate, and then the first substantially inelastic cable traveling back to the top of the semi-rigid femoral plate, and wherein the first substantially inelastic cable is routed through a tensioning mechanism
   and wherein a femoral loop portion of the first substantially inelastic cable, which extends from the crossover point over the semi-rigid femoral plate and back to the cross-over point, and a tibial loop portion of the first substantially inelastic cable, which extends from the crossover point over the semi-rigid tibial plate and back to the cross-over point, are configured such that a lengthening of the tibial loop portion of the first substantially inelastic cable results in a corresponding shortening of the femoral loop portion of the first substantially inelastic cable, and further wherein a corresponding tightening force resulting from the shortening of the femoral loop portion of the first substantially inelastic cable draws the semi-rigid femoral plate and the back plate closer together, and provides a radial force along the tibial loop portion of the first substantially inelastic cable directed toward the center of the tibial loop portion.

2. The knee brace of claim 1 wherein the tensioning mechanism comprises a single mechanism mounted to the front of the semi-rigid femoral plate and wherein the first substantially inelastic cable enters and exits from opposing sides of the tightening mechanism.

3. The knee brace of claim 1 further comprising a second cable coupled to the semi-rigid femoral plate and crosses the femoral and tibial pivot points and is coupled to the semi-rigid-tibial plate, wherein tension in the second cable inhibits the semi-rigid tibial plate from laterally bending or rotating relative to the semi-rigid femoral plate around an axis generally perpendicular to the natural axis of knee rotation.

4. The knee brace of claim 1 wherein the first substantially inelastic cable is attached to the semi-rigid tibial plate.

5. The knee brace of claim 1 wherein the first substantially inelastic cable includes cable segments coupled together.

6. The knee brace of claim 1 further comprising a locking system coupled to the semi-rigid femoral plate, the locking system configured to secure the first substantially inelastic cable to the semi-rigid femoral plate.

7. The knee brace of claim 1 wherein the differential force urges the back plate closer to the semi-rigid tibial plate and closer to the semi-rigid femoral plate.

* * * * *